United States Patent
Kennard

(10) Patent No.: US 8,608,473 B2
(45) Date of Patent: Dec. 17, 2013

(54) IMMEDIATE PROVISIONAL IMPLANT

(75) Inventor: Don Kennard, Yorba Linda, CA (US)

(73) Assignee: Nobel Biocare USA, Inc., Yorba Linda, CA (US)

( * ) Notice: Subject to any disclaimer, the term of this patent is extended or adjusted under 35 U.S.C. 154(b) by 2622 days.

(21) Appl. No.: 10/691,470

(22) Filed: Oct. 22, 2003

(65) Prior Publication Data

US 2004/0137406 A1  Jul. 15, 2004

Related U.S. Application Data

(62) Division of application No. 09/551,000, filed on Apr. 18, 2000, now Pat. No. 6,655,962.

(60) Provisional application No. 60/149,642, filed on Aug. 17, 1999.

(51) Int. Cl.
*A61C 8/00* (2006.01)

(52) U.S. Cl.
USPC .......................................................... 433/174

(58) Field of Classification Search
USPC ................................................. 433/172–176
See application file for complete search history.

(56) References Cited

U.S. PATENT DOCUMENTS

| | | | |
|---|---|---|---|
| 3,466,748 A | 9/1969 | Christensen | |
| 4,906,191 A | 3/1990 | Soderberg | |
| 5,074,790 A * | 12/1991 | Bauer | 433/174 |
| 5,259,398 A * | 11/1993 | Vrespa | 128/898 |
| 5,312,255 A | 5/1994 | Bauer | |
| 5,520,540 A * | 5/1996 | Nardi et al. | 433/172 |
| 5,556,280 A | 9/1996 | Pelak | |
| 5,795,160 A * | 8/1998 | Hahn et al. | 433/174 |
| 5,906,489 A | 5/1999 | Khazzam et al. | |
| 6,312,260 B1 | 11/2001 | Kumar et al. | |
| 6,325,628 B1 | 12/2001 | Morgan | |
| 6,447,295 B1 | 9/2002 | Kumar et al. | |
| 6,716,030 B1 * | 4/2004 | Bulard et al. | 433/174 |

FOREIGN PATENT DOCUMENTS

| | | |
|---|---|---|
| DE | 3918309 A1 | 6/1989 |
| WO | WO 99/29256 | 6/1999 |
| WO | WO 9929256 * | 6/1999 |

OTHER PUBLICATIONS

Dec. 19, 2000 International Search Report, Application No. PCT/US 00/22395, 2 pages.

* cited by examiner

*Primary Examiner* — Sunil K Singh
(74) *Attorney, Agent, or Firm* — Knobbe, Martens, Olson & Bear LLP

(57) ABSTRACT

An immediate provisional implant is provided, and method of use therefor, that serves to protect permanent dental implant anchors and overlying tissue during the healing and osseointegration process. Potentially damaging forces resulting from patient use of a temporary prosthesis during the osseointegration period are carried by the immediate provisional implant, rather than impinging upon non-osseointegrated permanent implant anchors or overlying tissue. The immediate provisional implants are self-threading and are inserted in osteotomies located near permanent dental implant anchors. The temporary prosthesis is removed after a period allowed for osseointegration of the permanent implant anchors, and the provisional implants can also be removed at the same time. The immediate provisional implants are non-linearly tapered from a maximum thread diameter near the bone surface to a more narrow distal end, providing immediate stability without the benefit of osseointegration.

20 Claims, 16 Drawing Sheets

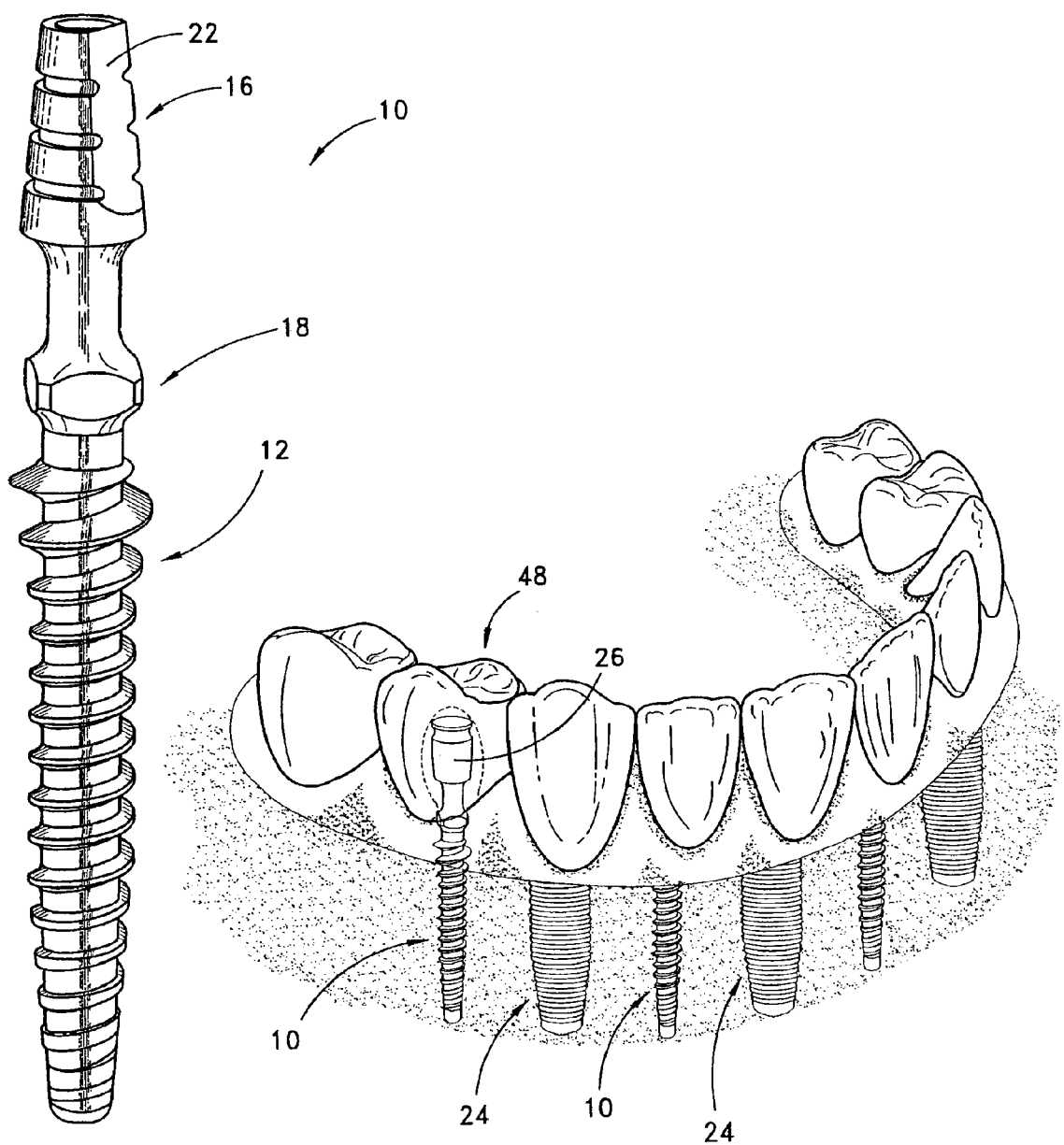

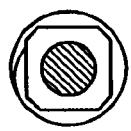
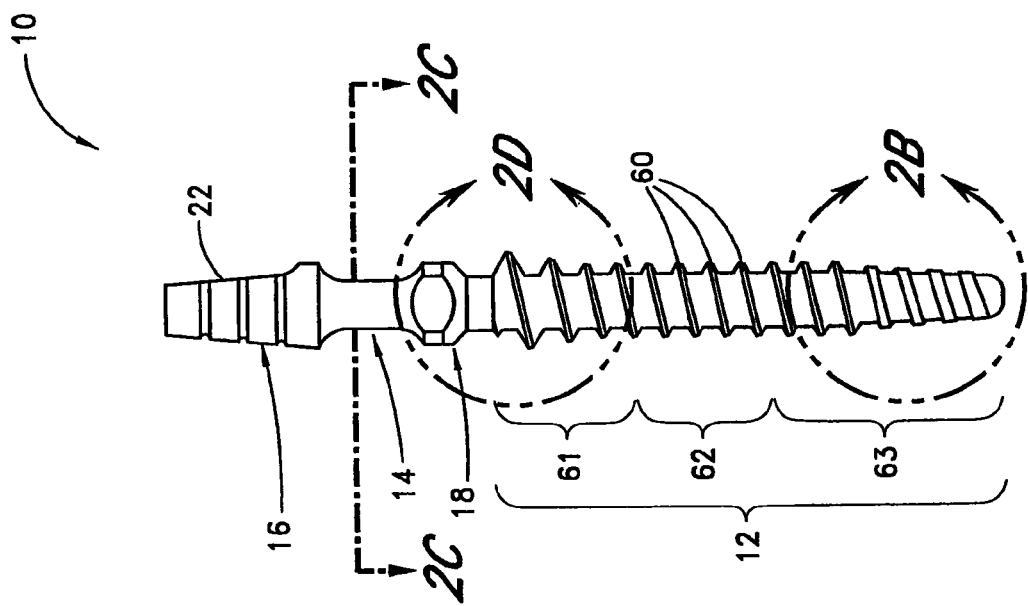
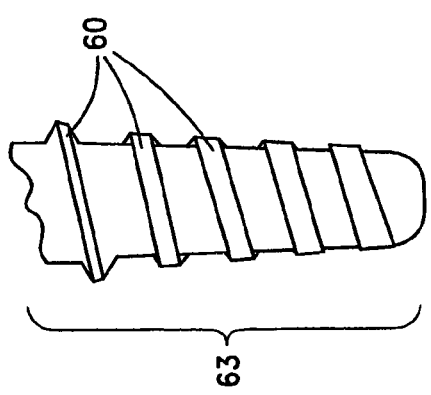

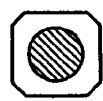
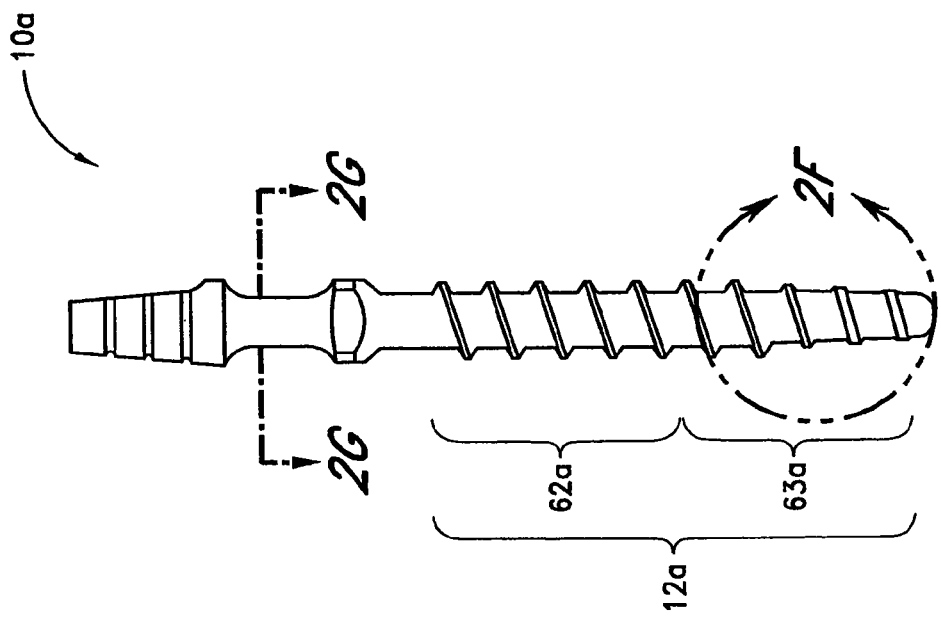
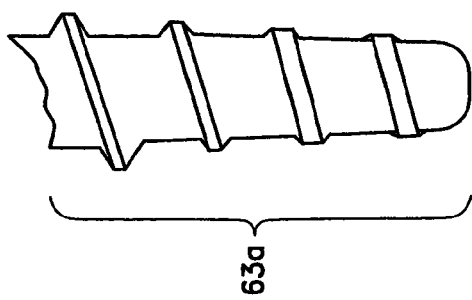

IMMEDIATE PROVISIONAL IMPLANT

REFERENCE TO RELATED APPLICATION

This application is a divisional of U.S. patent application Ser. No. 09/551,000, filed Apr. 18, 2000 now U.S. Pat. No. 6,655,962, which claims the priority benefit under 35 U.S.C. §119(e) from provisional Application No. 60/149,642, filed Aug. 17, 1999.

FIELD OF THE INVENTION

The present invention relates generally to dental implants and, more particularly, to an immediate provisional implant that allows for fitting a fixed, provisional prosthesis after first stage surgery.

BACKGROUND OF THE INVENTION

Dental implants are placed in the jaw to provide support for a dental restoration, fixed bridge or removable partial denture. Dental implants provide good chewing function and also improve the patient's cosmetic appearance, thereby allowing the patient to smile, speak, and interact with others with greater confidence.

One type of dental implant widely used in the industry is a "threaded" implant. Threaded implants have an externally threaded body segment, which is screwed into a pre-drilled hole (i.e., an osteotomy), in the patient's upper or lower jawbone. Typically, the threaded implant body is formed with a central threaded socket accessible through the overlying gum tissue for receiving and supporting one or more dental attachments or components. Types of attachments and components that are received by the central socket include healing caps, impression copings and abutments. In turn, some of these attachments and components are useful to fabricate and/or to support a prosthodontic restoration, fixed bridge or partial denture. Exemplary implant constructions are disclosed in U.S. Pat. No. 4,645,453 to Nizick, U.S. Pat. No. 5,074,790 to Bauer and U.S. Pat. No. 5,312,255 to Bauer.

Dental implants are typically packaged as an assembly including all the tools necessary for the insertion of the implant into an osteotomy formed in the jaw. A typical threaded implant assembly includes a threaded implant body, an implant carrier, an insertion post, a coupling screw and a healing cap. The implant carrier, insertion post, and coupling screw are tools which are used for the insertion of the implant body. Typically, the implant carrier, insertion post and coupling screw are discarded after the implant body has been inserted into the osteotomy.

During the insertion procedure, the insertion post is securely coupled to the top of the implant body. The insertion post is held in place by a coupling screw, which traverses a central through-cavity in the insertion post and is threaded into the central threaded socket in the implant body. Typically, the bottom end of the insertion post has a hexagonal cavity that irrotationally mates with a hexagonal protrusion on the top of the implant, thereby preventing any relative rotation between the insertion post and implant body.

The coupling screw and insertion post are releasably coupled to an implant carrier. The implant carrier provides the dental practitioner with a means to grip and manipulate the assembly during the initial implantation procedure. Typically, the implant carrier includes a generally hexagonal internal passage at its bottom end which mates with a generally hexagonal outer surface of the insertion post. This allows torque applied to the carrier to be transferred, via the insertion post, to the threaded implant body. The dental practitioner uses the implant carrier to manipulate the implant body into the proper location within the jaw.

In use, the first step of the implantation procedure usually involves making an incision in the patient's gum. A portion of the gum is then folded back and an osteotomy is drilled in the jawbone. The diameter of the osteotomy is equal to or slightly smaller than the diameter of the implant body. The implant carrier is then used to transport the threaded implant assembly to the surgical site. The implant carrier is used by the practitioner to manipulate the implant body into the correct position and then to partially screw the implant body into the osteotomy. Once the implant body has been initially placed in the osteotomy and tightened manually, the carrier is then pulled and/or loosened and removed from the dental implant assembly, leaving only the insertion post and coupling screw in engagement with the threaded implant body. A suitable wrench or dental hand piece is then used to engage the insertion post and drive the implant to its final depth within the osteotomy. The coupling screw is then unscrewed from the implant body, thereby allowing extraction of the insertion post and coupling screw from the patient's mouth. Next, a healing cap is screwed into the exposed socket of the implant to cover the implant socket. The healing cap protects the implant socket against tissue in-growth during the initial healing period, and also prevents the entry of bacteria or other contaminants into the exposed central socket of the implant. Typically, the healing cap is housed in a cavity at the top of the implant carrier and is secured with a paper barrier until needed.

The insertion of the implant body and healing cap is followed by an initial healing period in which the bone is allowed to surround and retain the implant (i.e., "osseointegrate" with the implant) and the gum tissue is allowed to heal over the implant body and healing cap. For implants placed in the mandible, healing typically requires about three months; for implants in the maxilla, the healing period typically requires about six months.

After sufficient osseointegration has occurred, the gum tissue is re-opened by making an incision and the gum tissue is once again folded back to remove the healing cap from the implant body. To remove the healing cap from the implant body, torque is applied to the healing cap to rotate the healing cap out of the implant socket. Typically, a removal tool with a hexagonal tip is inserted into a corresponding mating hexagonal recess located in the top center of the healing cap. Great care must be used to rotate the healing cap without also rotating the implant body. Any movement of the implant body relative to the osteotomy during the removal of the healing cap could damage the osseointegration between the implant body and the jawbone. Damage to the osseointegration is very undesirable and could endanger the entire dental restoration process by destabilizing the implant. In addition, any movement of the implant body could create unwanted gaps or spaces between the implant body and jawbone which could lead to infection by bacteria or other contaminants. After the healing cap has been unscrewed and removed from the implant body, a suitable healing abutment is attached. The healing abutment extends through the gum tissue overlying the implant site.

A second healing period then ensues in which the gum tissue is allowed to heal around the post-osseointegration healing abutment. Typically, this second healing period lasts from four to eight weeks. After this second healing period, the healing abutment is removed from the implant. Typically, an impression is taken of the patient's mouth to fabricate a prosthesis or dental restoration. An abutment supporting the final restoration is attached to the implant. Lastly, the restoration is cemented or screwed to the abutment and/or implant to complete the placement of the prosthodontic restoration in the patient's mouth.

The threaded dental implants described above, as well as other dental implants, such as "cylindrical" implants, require healing periods of three to six months or more. In the meantime, it has been desirable in the past to provide patients with temporary partial dentures or full dentures until the final restoration is in place. However, mastication forces on conventional temporary partial dentures and full dentures can harm or otherwise irritate the gum tissues overlying conventional submerged implants, bone grafts or tissue grafts and/or can also disturb the implants.

Accordingly, methods and structures are needed to provide protection to subcutaneous implants and the adjacent tissues from impinging mastication forces and moments during the healing period.

SUMMARY OF THE INVENTION

Briefly stated, the aforementioned needs are satisfied by a new method of providing permanent dental prosthesis that utilizes one or more immediate provisional implants to support a temporary prosthesis during the healing phase after conventional endosseous implant surgery. In particular, the immediate provisional implant(s) are positioned between conventional permanent implants, and are used to support temporary dental prostheses while the permanent implants are allowed to osseointegrate. Desirably, the immediate provisional implants are structured to satisfy the particular needs of this temporary support.

The immediate provisional implant (IPI) system of the present invention is advantageously designed to allow implant surgeons to place titanium alloy provisional implants in either the mandible or maxilla. Implant therapy often requires the patient to wear a provisional restoration for an extended period of time during the healing phase. An important advantage of the IPI System is to be able to deliver a more stable, temporary fixed prosthesis at the time of implant placement. This prosthesis removes the load from the soft tissues overlying subcutaneous implants surgically placed simultaneously or at about the same time (i.e., immediately prior or subsequent to implanting the immediate provisional implants) at adjacent sites during stage-one surgery.

By carrying the load of the temporary prostheses, the provisional implants allow improved healing of the permanent implant sites and at the same time provide the patient an aesthetic, functional, fixed provisional prosthesis after stage-one surgery. This is especially important for grafted sites. Placement of provisional implants enables the patient to wear an aesthetic, stable, fixed provisional prosthesis. This can improve treatment acceptance of grafting and implant procedures. Such use of provisional implant dental restorations also minimizes the risk of possible bone atrophy and bone shifting caused by reduced bone loading during the healing period.

The diameter of each provisional implant is preferably narrow enough to allow it to be placed between permanent implants at the time of surgery. The immediate provisional implant width or diameter is preferably between about 1 mm and 3.5 mm, more preferably less than about 3 mm, and in the illustrated embodiments the implants have a maximum outer thread diameter between about 2 mm and 2.8 mm (preferably tapered along its length). A non-linear taper is preferred in another embodiment, whereby the thread diameter rapidly increases near the top of the threaded segment adjacent the crestal bone. Advantageously, this allows that region of the threaded body which is mated with the denser cortical bone to resist applied moments, with less damage to the less dense bone beneath. The non-linear tapered implant may be generally characterized as having a flared upper segment having a relatively large taper angle, a generally cylindrical intermediate segment and a lower tapered segment having a relatively small taper angle.

The overall length of the preferred immediate provisional implant is preferably greater than about 17 mm, more preferably greater than about 20 mm, and most preferably about 22 mm. This length includes an anchor segment designed to be anchored in cortical bone to a depth greater than that of adjacent permanent implants. This anchor segment is threaded in the illustrated embodiments, and is preferably 12-16 mm (14 mm preferred), sufficient to support the forces on a provisional prosthesis. A flared taper at the proximal end of the implant facilitates enhanced engagement of the cortical bone layer, giving the immediate provisional implant according to the invention better initial stability without osseointegration. This allows the underlying conventional implant or graft to heal without premature loading.

One preferred embodiment of a provisional implant according to the invention also preferably includes an integral extension from the anchoring segment, preferably greater than about 3 mm, more preferably greater than about 5 mm, and most preferably about 7.34 mm. The extension includes a portion extending above the crestal bone and serving to receive a temporary dental prosthesis or restoration.

The immediate provisional implant is preferably of single piece construction and is preferably fabricated from titanium alloy for strength. The extension from the anchoring segment preferably includes an abutment portion and an intermediate bendable neck to allow for abutment parallelism. The hourglass shape of such a neck not only provides the desired flexibility, but can also help prevent migration of soft tissue over the implant abutment.

The integral implant and abutment design provides predictable retention and support of the temporary prosthesis. Machined titanium copings, which become integrated into the final prosthesis, engage the tapered design of the abutment resulting in retention, stability and a precise margin fit of the temporary restoration. The provisional restoration may be fabricated by the restorative dentist or clinician directly over the titanium coping. Optional analogs are also preferably available if it is preferred or indicated to fabricate the restoration using a laboratory model and a cast stone replica of the patient's mouth/jaw.

Advantageously, the IPI System can be used for fully and partially edentulous patients. Two to three immediate provisional implants can be used for a partially edentulous patient. On average, a fully edentulous case employs four-to-six immediate provisional implants (preferably, five in the maxilla). The immediate provisional implants are preferably placed at a minimum distance of about 3.0 mm from conventional submerged root form implants. The IPI System thus eliminates the need for temporary partial dentures that can otherwise harm or irritate conventional submerged implants or bone grafts. Once the permanent implants are fully healed and oseointegrated to the patient's jaw bone, the immediate provisional implants can be partially or fully removed with minimal discomfort to the patient. Patient acceptance for conventional implant procedures may increase due to the fact that the immediate provisional implant system allows them to leave the office after stage-one implant surgery with a fixed provisional or temporary restoration.

In accordance with one aspect of the invention, a method of providing permanent dental prosthesis to a patient who is at least partially edentulous includes providing a permanent implant within bone in a patient's mouth at a permanent implant site, and providing a provisional implant within the bone in the patient's mouth adjacent the permanent implant site.

In accordance with another aspect, a method provides a fixed, temporary dental prosthesis during a healing period for permanent implant osseointegration. The method includes implanting permanent implants in a bone within a patient's mouth. Provisional implants are also implanted in the bone at positions alternatingly adjacent the permanent implants. Each of the provisional implants includes an abutment protruding out of the bone. The temporary dental prosthesis is adhered to the abutments. After a healing period, during which the permanent implants osseointegrates, the temporary dental prosthesis is removed from the abutments.

In accordance with another aspect of the invention, a system provides an interim dental prosthesis while allowing osseointegration of a permanent implant. The system includes at least one permanent implant for anchoring within a patient's mouth. The system also includes a plurality of provisional implants for anchoring adjacent the permanent implant. A temporary dental prosthesis is configured to be supported upon the provisional implants.

In accordance with another aspect of the invention, a system provides an immediate provisional dental implant. The system includes a plurality of provisional dental implants. The implants each include a threaded body segment, a neck segment integrally formed with and extending from the body segment, and an abutment integrally formed with and extending from the neck segment. The body segment preferably has a maximum width no more than about 3.5 mm. The neck segment includes a torque accepting feature. The system also includes an osteotomy drill with a diameter less than the maximum width of the threaded body. A torque-supplying driver tool is adapted to engage with the torque-accepting feature of each provisional dental implant in order to impart rotation for self-screwing the provisional implant into an osteotomy drilled by the osteotomy drill.

In accordance with another aspect of the invention, an integrally-formed immediate provisional dental implant extends along an implant axis. The implant includes an abutment adapted to bond with a dental prosthesis, a flexible neck segment connected to the abutment, and a threaded body segment. The body segment has threads extending helically about the implant axis. The thread diameter tapers non-linearly from a maximum adjacent the neck segment to a minimum at a distal end. For purposes of summarizing the invention and the advantages achieved over the prior art, certain objects and advantages of the invention have been described herein above.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and its essential features and advantages, certain preferred embodiments and modifications thereof will become apparent to those skilled in the art from the detailed description herein having reference to the figures that follow, of which:

FIG. 1 is a side view of an immediate provisional implant having features in accordance with one embodiment of the present invention;

FIGS. 2A-2D are scale side and sectional views, showing one embodiment of the immediate provisional implant of FIG. 1, particularly suited for cortical engagement;

FIGS. 2E-2G are scale side and sectional views, showing another embodiment of an immediate provisional implant having features in accordance with the present invention;

FIG. 3 is a perspective view of the immediate provisional implant of FIG. 1 implanted into a patient's mandible;

DETAILED DESCRIPTION OF THE PREFERRED EMBODIMENTS

Figure 2D:
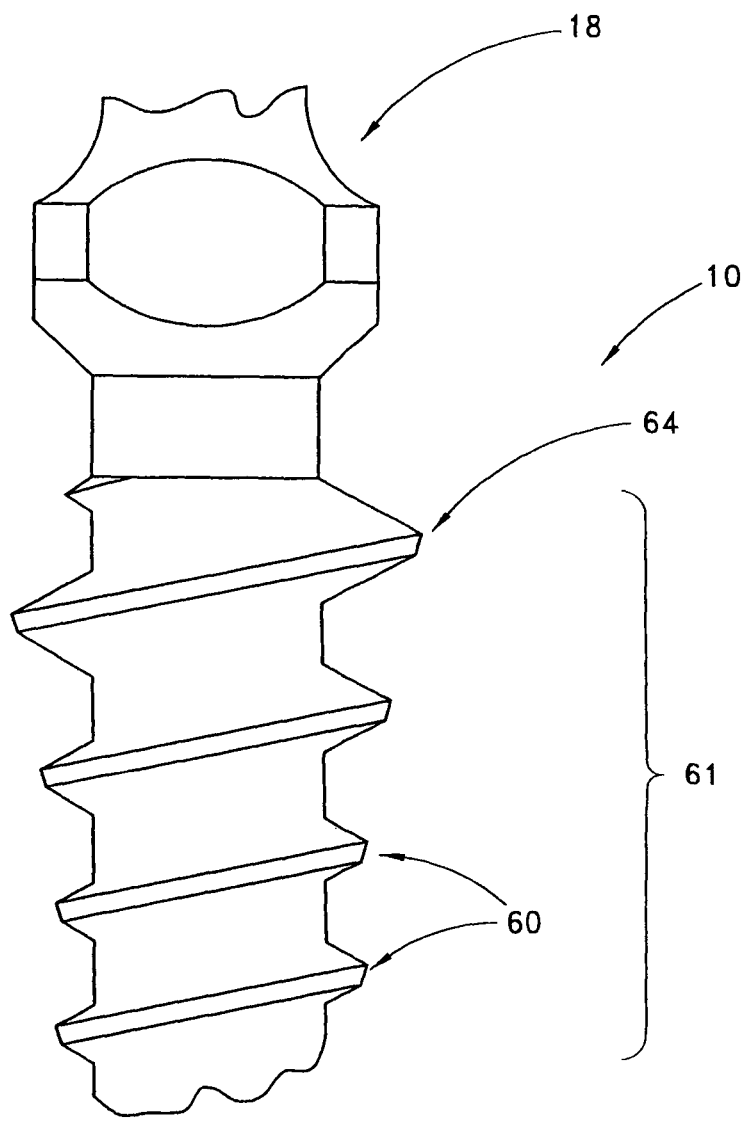

FIGS. 1 and 2A illustrate an immediate provisional implant 10 having features according to one preferred embodiment of the present invention. As shown in FIG. 2A, the implant 10 is preferably divided into four integral segments: a body segment 12, a neck segment 14, and a top segment or abutment 16. In the illustrated embodiment, the neck segment 14 includes a torque-accepting segment 18, particularly designed to engage with a torque-imparting tool. The body segment 12 includes mechanical structures to aid in anchoring the implant 10 within the mandible or maxilla, and is preferably threaded for this purpose. The body segment 12 thus represents the portion of the implant that is placed in either the mandible (see FIG. 3) or the maxilla. In the illustrated embodiment, the threading 60 extends in a helical path along the length of the body segment 12. The threads are preferably machined to have a thread interval or "pitch" of about 1 mm to 1.5 mm (1.17 mm illustrated) near the top of the body segment 12, varying to about 0.6 mm to 0.9 mm (0.84 mm illustrated) at the lower end on the body segment. The threads 60 have flat top lands with a nominal width of about 0.10 mm to 0.15 mm near the top of the body segment 12.

In the particular preferred embodiment of FIGS. 2A-2D, the body segment 12 has three sections or sub-regions 61, 62, and 63, distinguished according to how the thread diameter and depth varies in those sub-regions. The intermediate sub-region 62 is preferably a region of approximately constant thread diameter of about 1.8 mm to 2.2 mm (about 2.032 mm in the illustrated embodiment) and approximately constant thread depth of about 0.22 mm to 0.28 mm (about 0.254 mm in the illustrated embodiment). The lower sub-region 63, best seen from FIG. 2B, preferably extends to the distal most end of the body segment 12. The lower sub-region 63 is preferably characterized by a reducing thread diameter and thread depth toward the distal end, producing a slope or angle to the implant axis. Preferably, the thread top lands produce a slope of about 1°-10°, more preferably 3°-7° (about 5° in the illustrated embodiment). The troughs define a smaller slope, preferably 0.5°-3° (about 2° in the illustrated embodiment), such that the thread depth becomes shallower toward the distal end.

The upper sub-region 61 of the illustrated embodiment is preferably designed to engage the cortical bone, and is shown in more detail in FIG. 2D. The thread diameter and thread depth preferably tapers from the proximal to distal end in the upper sub-region 61 greater than the tapering in the lower sub-region 63. Preferably, this taper in thread diameter is characterized by a slope relative to the implant axis of about 6°-14°, more preferably about 8°-12° and, most preferably, about 10° as in the illustrated embodiment. The maximum thread diameter is preferably less than about 3.5 mm, more preferably less than about 3 mm (2.72 mm in the embodiment of FIG. 2D). The proximal thread 64, adjacent the top segment 16, also represents the maximum width of the immediate provisional implant 10. The maximum thread depth, also occurring adjacent the neck segment 14, is preferably between about 0.5 mm and 0.7 mm (0.6 mm in the illustrated embodiment).

Alternatively, FIGS. 2E-2G illustrate another preferred embodiment of an immediate provisional implant 10a having an extended substantially constant-diameter or cylindrical section 62a, without the flared upper region previously described. For convenience of description and ease of understanding like reference numerals are used to designate like elements. In accordance with this embodiment, the maximum thread diameter is less than about 2.5 mm, and is about 2 mm in the illustrated embodiment. The second embodiment is otherwise substantially similar to the provisional implant of FIGS. 2A-2D.

Referring again to FIG. 2A, the torque-accepting segment 18 is located in the lower region of the neck segment 14, shown located about 1 mm from the largest thread 64. The torque-accepting segment 18 is preferably located below the top segment 16. Accordingly, the torque-accepting segment 18 facilitates removal of the immediate provisional implant. In the illustrated embodiments, the torque-accepting segment 18 is faceted and takes the shape of a square (see FIGS. 2C and 2G) with truncated corners, with a thickness between opposite faces of the square of about 2 mm.

The remainder of the neck segment 14 is preferably bendable to adjust the angle of the top segment or abutment 16. In the illustrated embodiment, the neck segment 14 has an hourglass shape and is illustrated with a length of 2.51 mm and a minimum width or diameter of 1.27 mm. The top segment 16 is preferably 3.81 mm long, and tapered by about 5°, with a maximum diameter of 2.36 mm at the distal end of top segment 16, adjacent the neck segment 14. Grooves 20 preferably extend partially around the top segment 16, except for a smooth flat surface 22, best seen in FIG. 1. The smooth surface 22 is preferably characterized by a flat plane or face intersecting and truncating the outer surface of the otherwise conical shape of the top segment 16, with the plane being 0.28 mm below the outer radius of the surface. This flat surface 22 provides for engagement with a wrench and also provides anti-rotation relative to a provisional abutment or restoration secured thereto.

Unlike the permanent implants, which are meant to be submerged below sutured soft tissue during a healing period after stage-one surgery, the neck segment 14 and abutment segment 16 are integrally formed with the anchoring or body segment 12. As noted above, these segments form an extension with a length preferably greater than about 3 mm, more preferably greater than about 5 mm (7.34 mm in the illustrated embodiment). This integral extension serves to allow attachment of a temporary prosthesis to the provisional implants 10 without further steps for connecting the extension.

FIG. 3 illustrates a mandible 23 of a patient having a plurality of immediate provisional implants 10 implanted therein, along with a plurality of "permanent" threaded implants 24. As shown, the provisional implants 10 are alternated with the permanent implants 24, which are meant to remain in place when the provisional implants are removed after the healing period. The provisional implants 10 are preferably substantially more narrow than the permanent implants 24, preferably less than half the width.

Figure 4A:
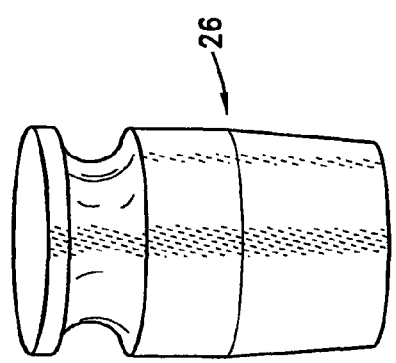
FIG. 4 is a perspective view of a coping having features according to one embodiment of the present invention.
Figure 4C:
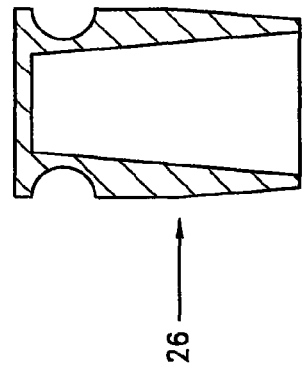
Figure 4B:
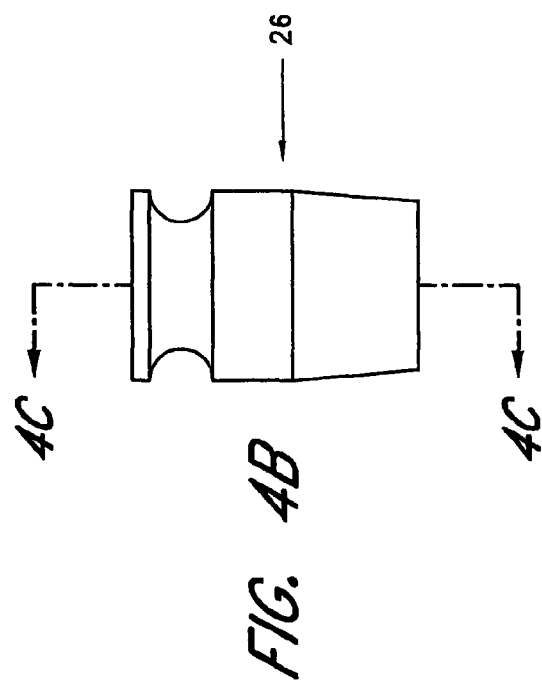

Each provisional implant 10 is shown with a coping 26 that mates with the top segment 16 of the implant 10. The coping 26 is also illustrated individually in FIGS. 4A-4C.

Figure 5:
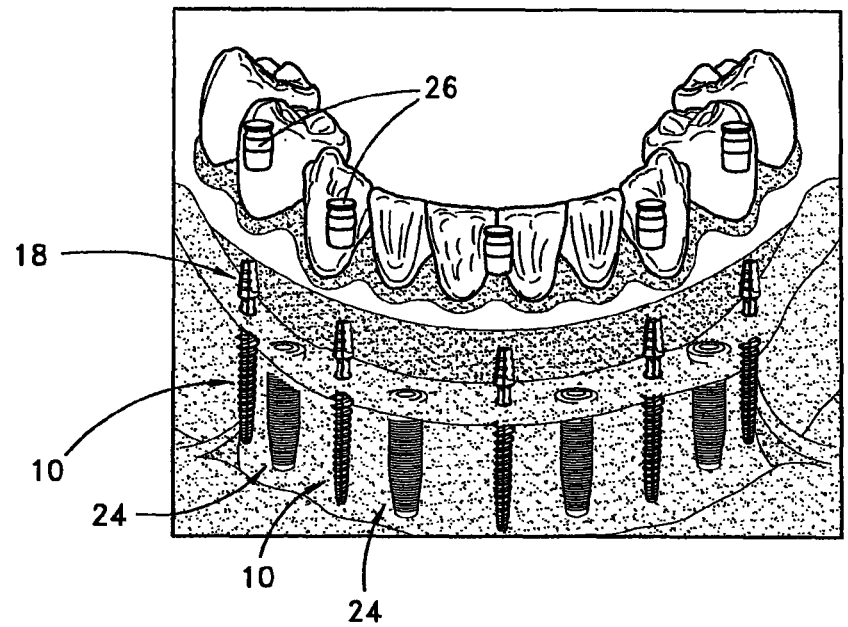
FIG. 5 is a perspective view of a plurality of immediate provisional implants implanted into a patient's mandible.

FIG. 5 illustrates another arrangement for the immediate provisional implants 10. It will be appreciated that other arrangements are contemplated, as would be determined based on the positioning of the implants 24 and other factors.

Figure 6:
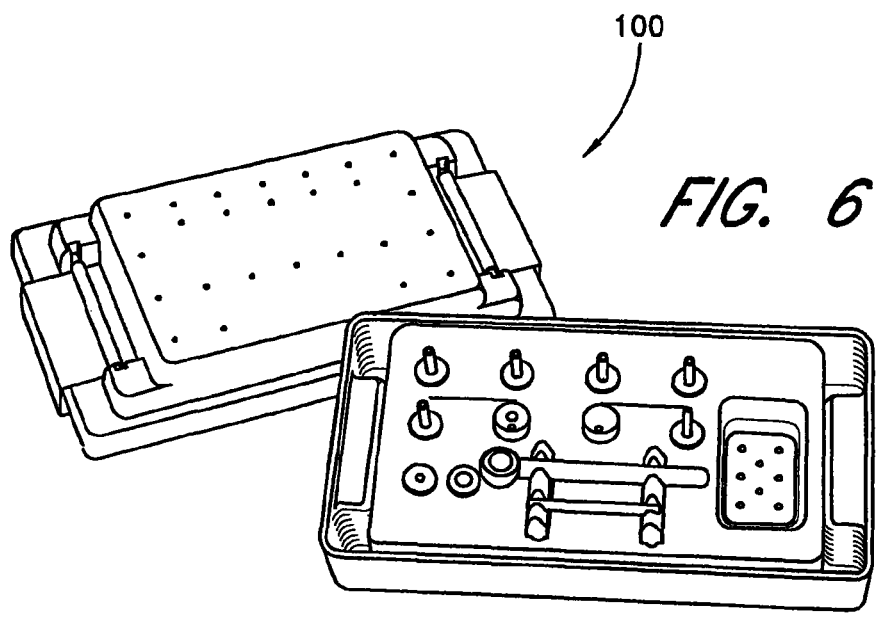
FIG. 6 is a perspective view of an immediate provisional implant system having features according to one embodiment of the present invention.
Figure 7:
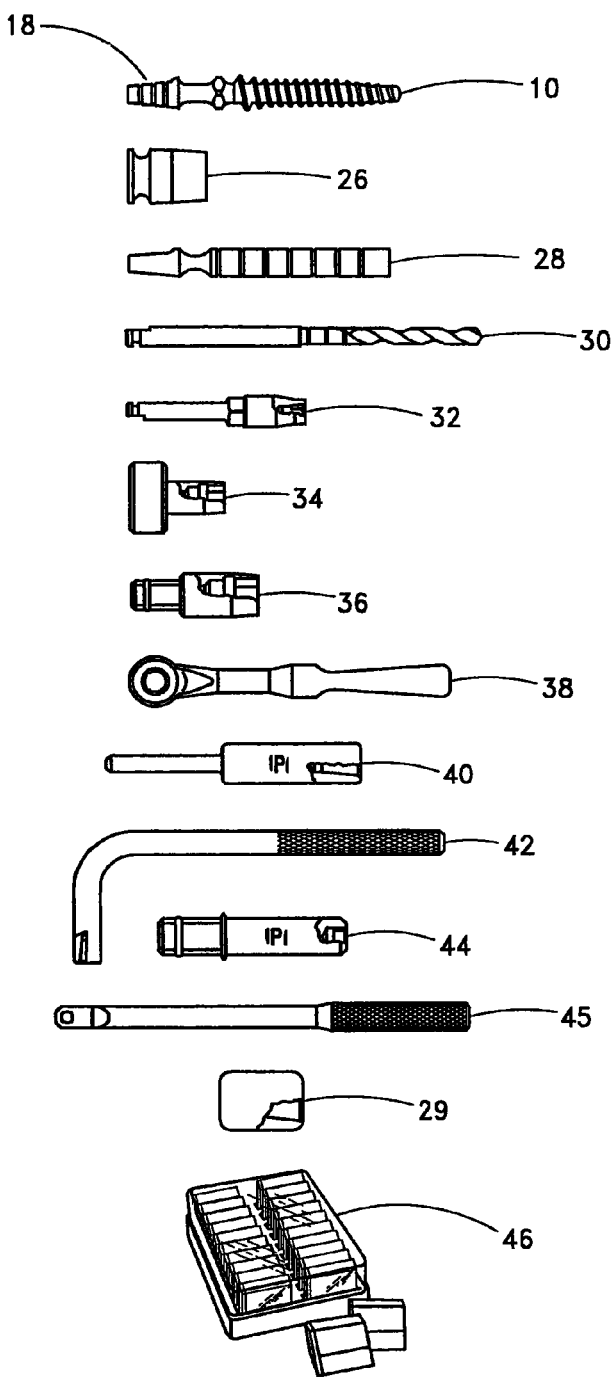
FIG. 7 is a detail side view of the preferred components comprising the immediate provisional implant system of FIG. 6.

FIGS. 6 and 7 illustrate one embodiment of the immediate provisional implant system. FIG. 6 shows an autoclavable kit 100 containing the tools for placement and removal of the immediate provisional implants. FIG. 7 shows the contents of the kit 100 in more detail. As shown in FIG. 7, the system includes the following: fifteen implants 10 and copings 26 (in three packs of five); optional analogs 28 and comfort caps 29 (also packaged in packs of five); a disposable twist drill 30; an insertion wrench 32; a hand wrench 34; a ratchet adapter 36; a ratchet 38; parallel pins 40; a bending tool 42; a retrieval tool 44; a stabilizer 45; and an organizer 46 for the packaged items. The packaged items 10, 26, 29 and the disposable twist drill 30 are desirably pre-sterilized. The torque-accepting segment 18 of the immediate provisional implant of FIGS. 1-2D is designed to mate with a torque-supplying tool like the insertion wrench 32 and/or hand wrench 34 that are shown in FIG. 7.

Figure 8A:
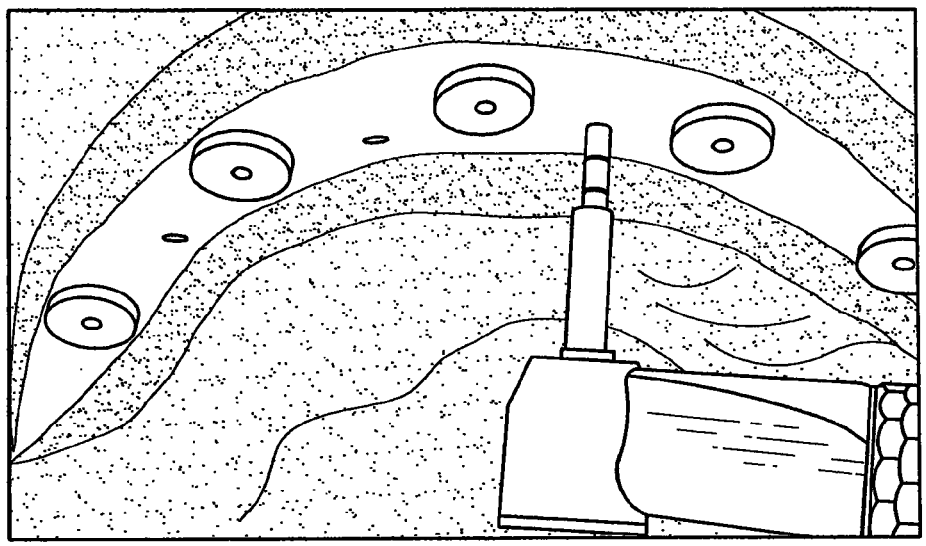
FIGS. 8A-8E illustrate initial steps for implanting immediate provisional implants in accordance with the preferred embodiments.

FIGS. 8A-8E illustrate a preferred placement procedure for the immediate provisional implant system, using the components described above. In step 1, as shown in FIG. 8A, it is first ensured that there is a minimum distance of 3 mm from the conventionally submerged permanent implants 24. Then, the cortical crestal bone 50 is penetrated preferably with a disposable twist drill 30 and the ratchet having a width smaller than the provisional implants 10 (1.5 mm shown). The drill 30 penetrates preferably to a depth of about 14 mm. Either the apical, buccal or lingual cortical bone is engaged to ensure implant stability.

Figure 8B:
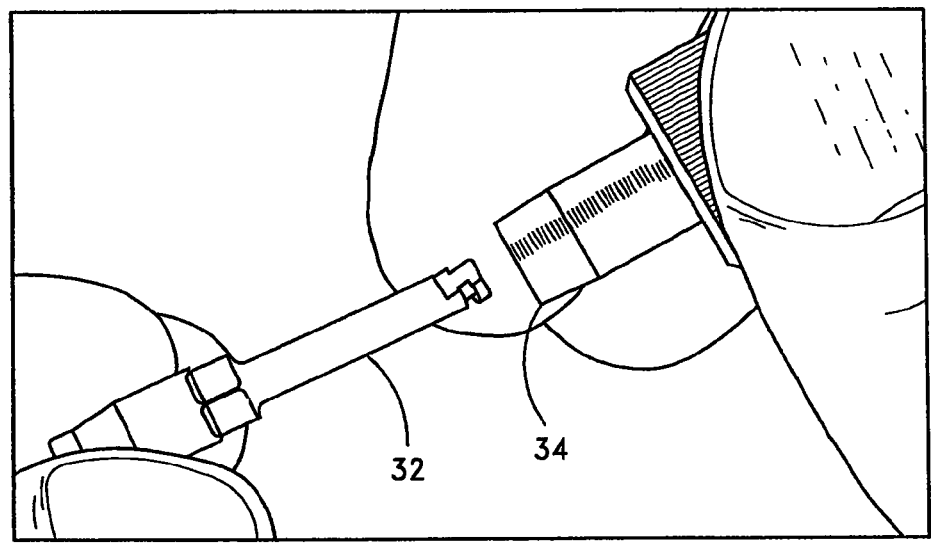
Figure 8C:
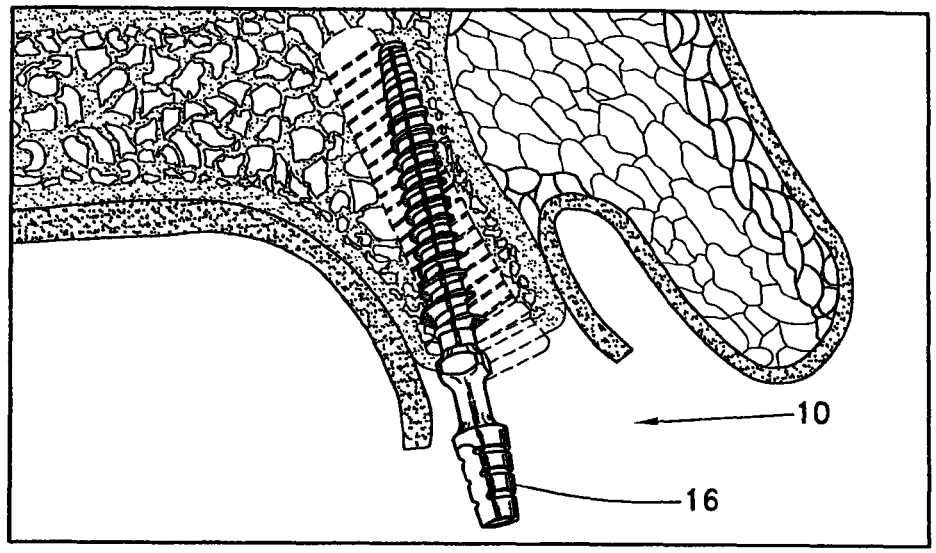
Figure 8D:
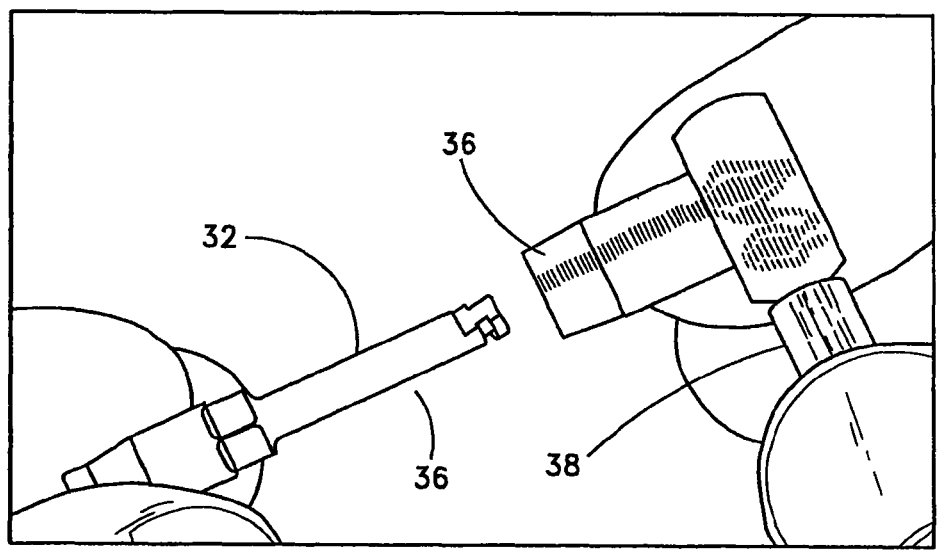
Figure 8E:
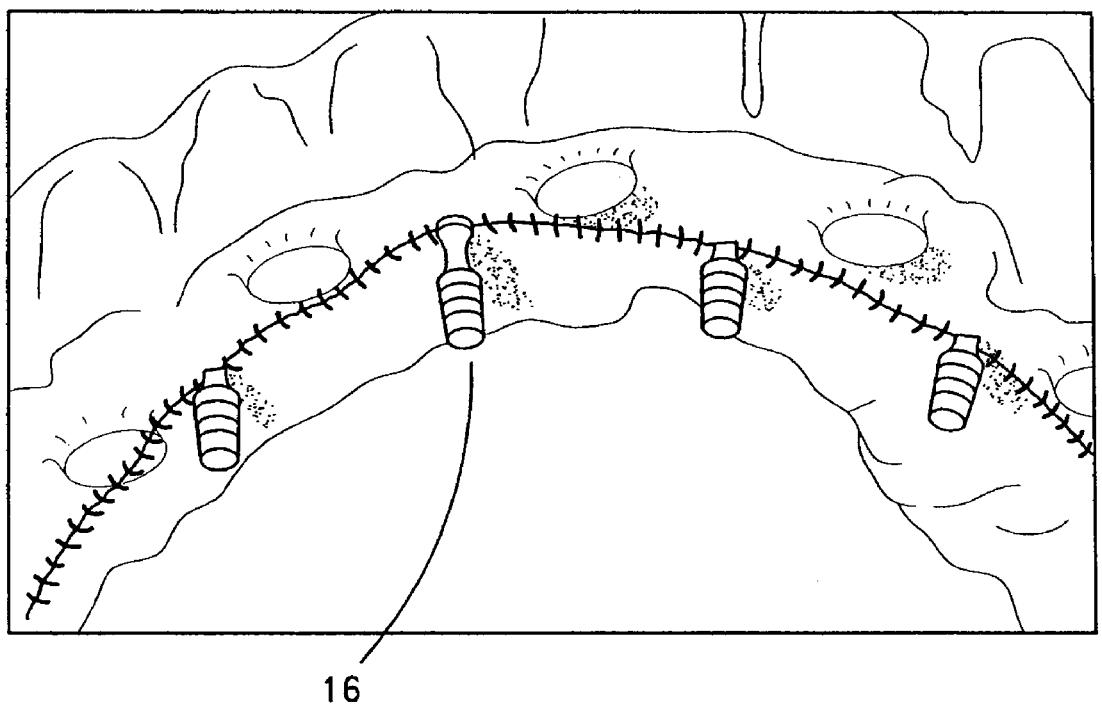

For step 2, as shown in FIG. 8B, the insertion wrench 32 is inserted into the hand wrench or handpiece 34. For step 3, the implant abutment 16 is placed into the insertion wrench 32 and the implant 10 is self threaded into the osteotomy until the shoulder of the implant 10 is even with the ridge, as shown in FIG. 8C. If the bone 50 is dense, the ratchet 38 with ratchet adapter 36 can be optionally employed. As shown in FIG. 8D, the ratchet adapter 36 is first inserted into the ratchet 38. The insertion wrench 32 is placed into the ratchet adapter 36 and step 3 proceeds as described above. For step 5, as shown in FIG. 8E, after the immediate provisional implants 10 are placed, the tissue is sutured, leaving the abutment segments 16 exposed.

Figure 9A:
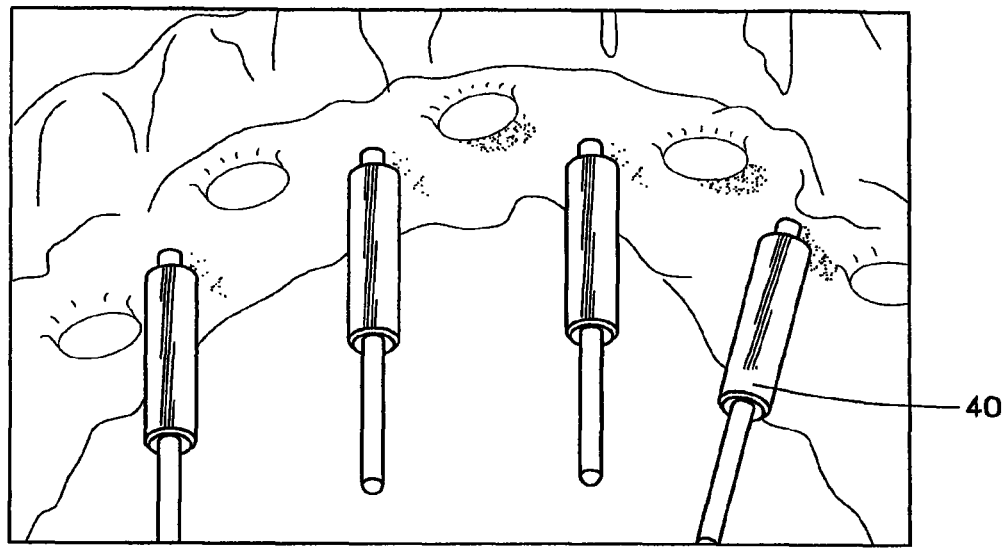
FIGS. 9A-9E illustrate further steps for providing temporary fixed prostheses over the immediate provisional implants of FIG. 8E, in accordance with a direct technique embodiment for fully edentulous patients.
Figure 9B:
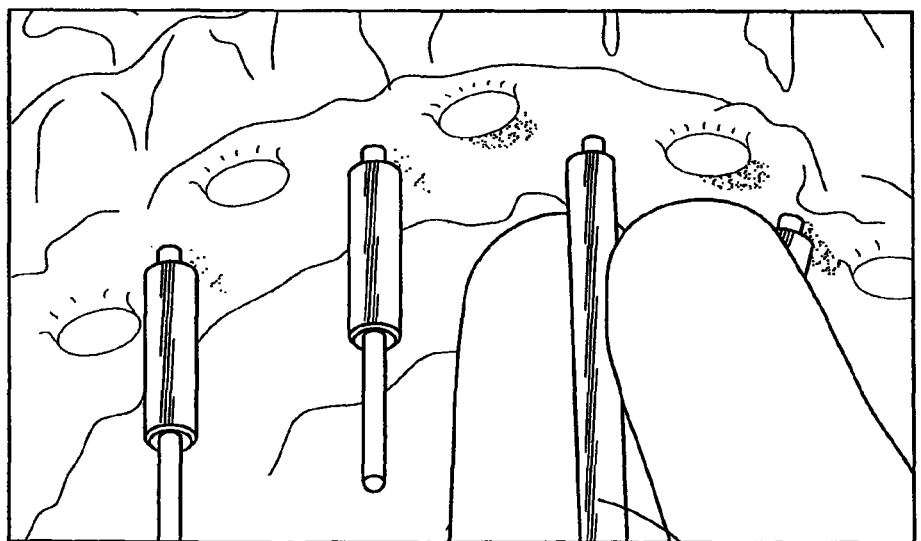

For the fully edentulous case, as illustrated in FIGS. 9A-9D, the five steps described above are followed by placing parallel pins 40 (step 6) onto the implants 10, as shown in FIG. 9A. This helps aid in visualizing orientation or parallelism of each immediate provisional implant with respect to the jawbone or other implants. As shown in FIG. 9B (step 7), the implants are preferably adjusted or bent at the neck of the implant using a bending tool 42 to achieve a desired orientation.

Figure 9C:
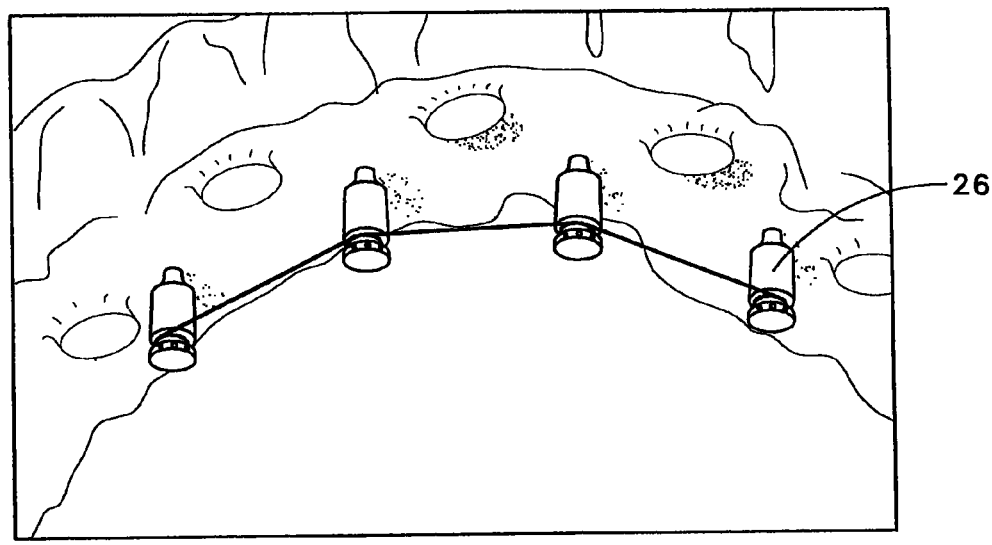
Figure 9D:
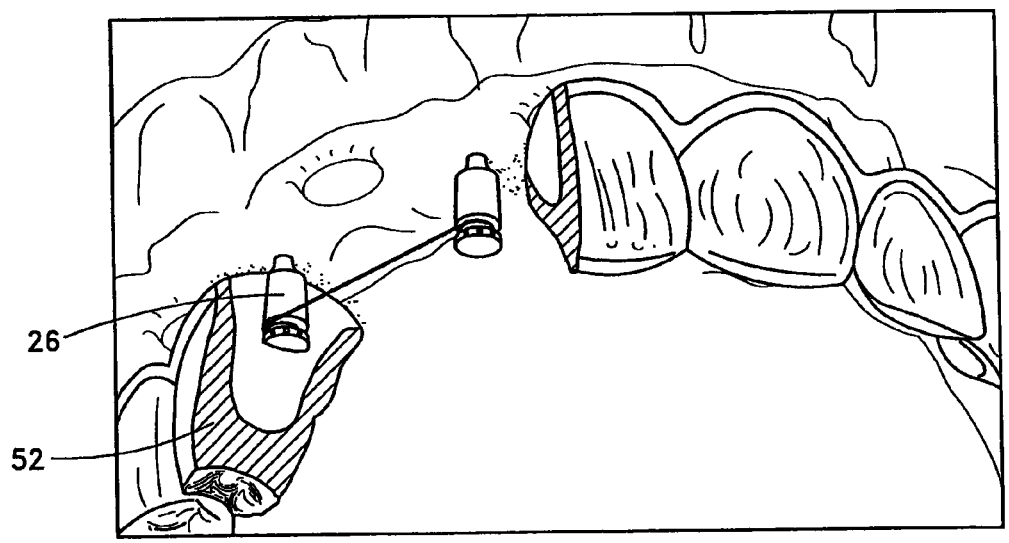

As shown in FIG. 9C (step 8), copings 26 are then placed over the implants. In step 9 (not shown), any exposed undercuts on the implant are blocked out. The soft tissue and sutures are lubricated with petroleum jelly. As shown in FIG. 9D, in step 10, autopolymerizing, tooth-colored acrylic, mixed to a pliable consistency, is placed into a processed acrylic shell 52 and placed over the copings 26. Desirably, the acrylic is moderately viscous so as to avoid being forced under the tissue onto the implant 10, hardening preferably only over the coping 26. The patient is instructed to close in centric relation occlusion. A prosthesis 54 is thereby formed, as shown in FIG. 9E.

Figure 9E:
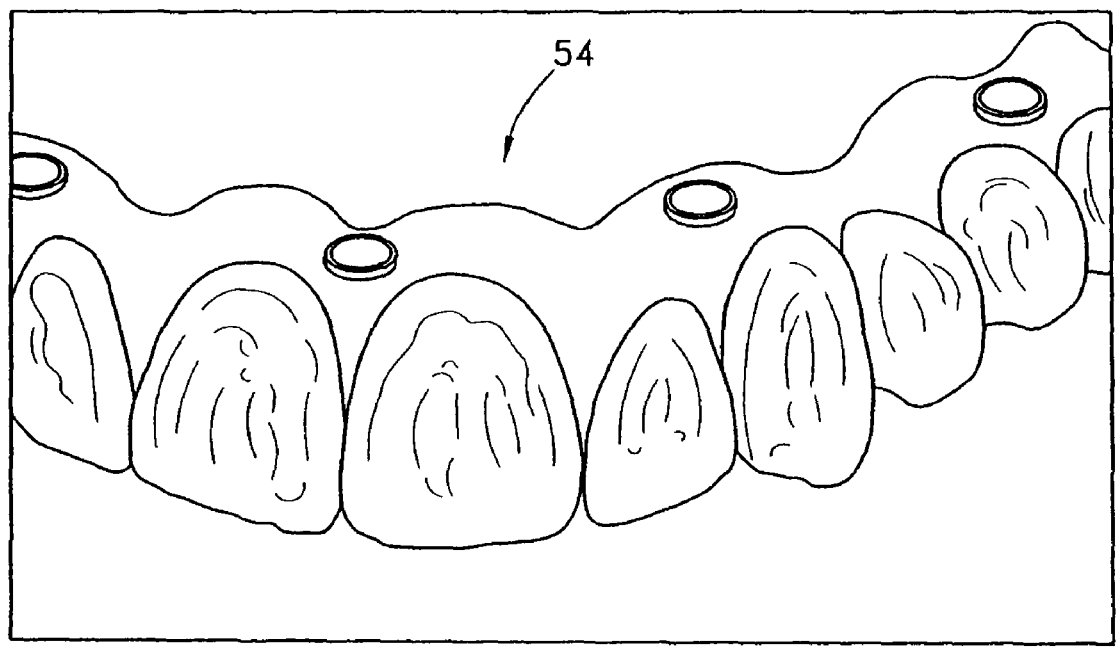

As shown in FIG. 9E, after the acrylic has hardened, the provisional prosthesis 54 is removed with the copings 26 secured in the prosthesis (step 11). If desired, excess acrylic can be removed from the prosthesis and the underside checked and cleared of any soft tissue impingements. The occlusion may also need to be refined and the provisional restoration removed, shaped and polished prior to affixation. Once suitably refined the restoration or provisional prosthesis 54 is preferably cemented into place using a suitable temporary adhesive, such as ImProv™ Temporary Cement (Cat. No. 4400) available from Nobel Biocare USA, Inc. of Yorba Linda, Calif.

Figure 10:
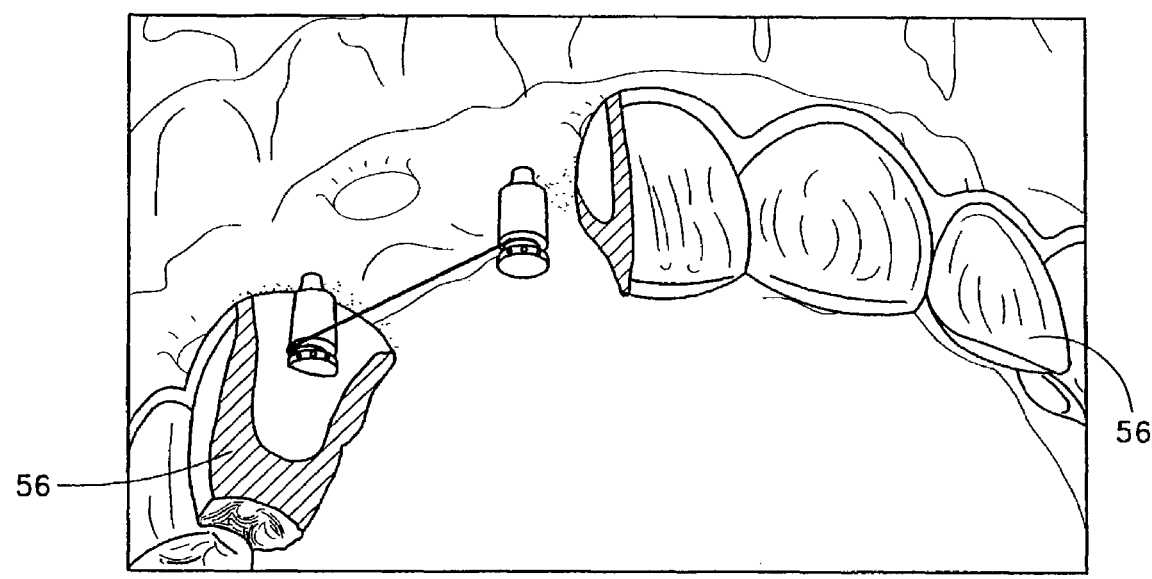
FIG. 10 illustrates a further step for providing temporary fixed prostheses over the immediate provisional implants of FIG. 9C, in accordance with another direct technique embodiment for fully edentulous patients.

In another embodiment, a direct technique is provided using a patient's existing denture 56. Steps 1 to 9 are completed as described above with respect to FIGS. 8A-9C. Then, in step 10a (not shown), flanges are removed from the patient's existing denture. The denture 50 is hollowed from second pre-molar to second pre-molar. In step 11a, autopolymerizing acrylic is placed in the hollowed out denture 56 and placed over the copings 26, as shown in FIG. 10. The patient is instructed to close in centric relation occlusion. After the material has set, the denture is removed and cleaned, trimming excess material, and polishing the denture and removing any soft tissue impingements. The denture 56 is then cemented in place using a temporary cement.

Figure 11A:
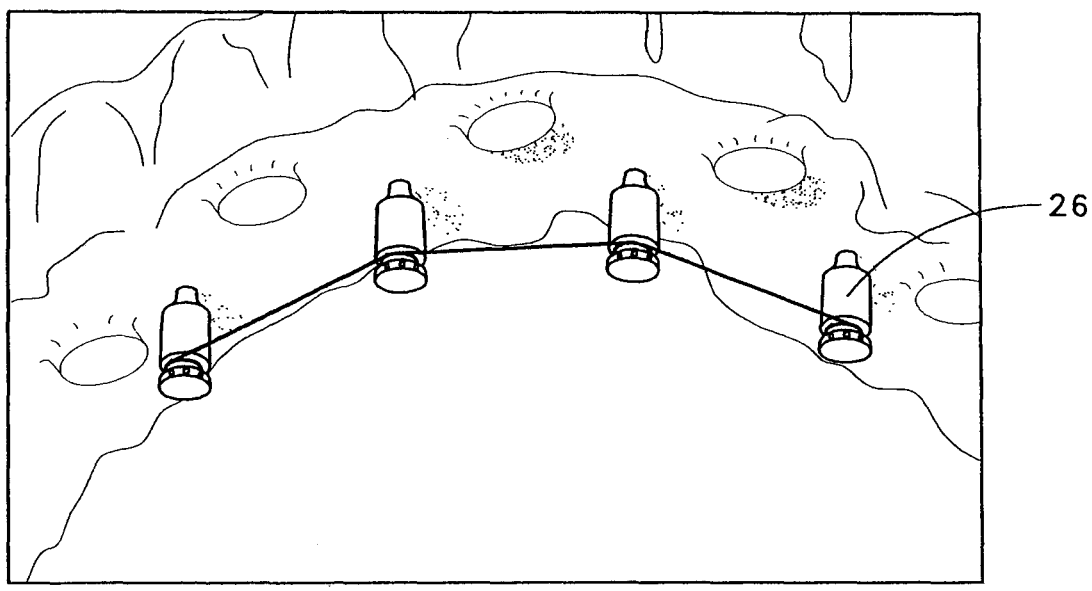
FIGS. 11A-11C illustrate further steps for providing temporary fixed prostheses over the immediate provisional implants of FIG. 9C, in accordance with an indirect procedure for fully or partially edentulous patients.
Figure 11B:
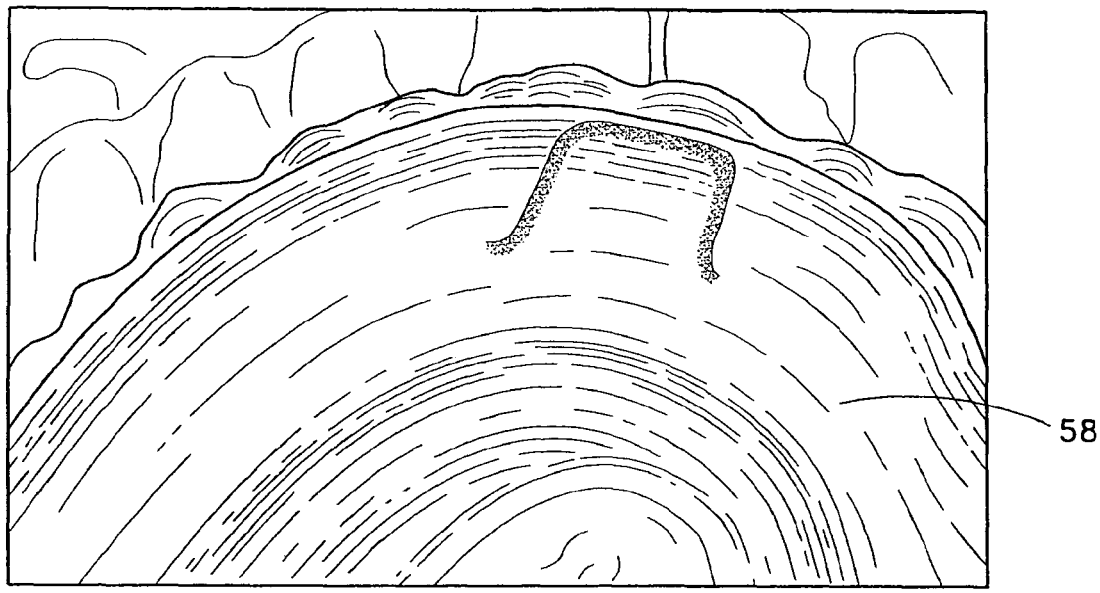
Figure 11C:
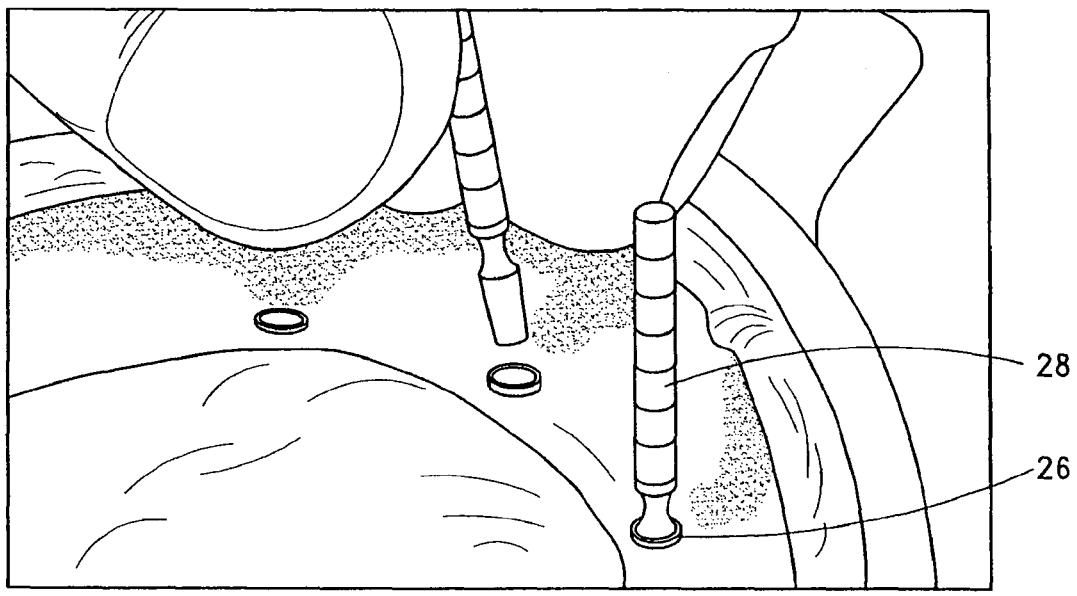

In another embodiment, an indirect procedure is provided for partially or fully edentulous cases. Steps 1 to 9 are first completed as described above. The copings 26 are placed onto the implants in step 10b, as shown in FIG. 11A. In step 11b, an impression is taken with a resilient impression material 58, as shown in FIG. 11B. A light body material is used at the implant/tissue interface. The impression 58 with copings 26 (FIG. 11A) is then removed. A bite registration is recorded and an impression of the opposing arch is taken. In step 13b, as shown in FIG. 11C, the immediate provisional implant analogs 28 are placed into the copings 26 and the impression is then poured in hard stone. The model is separated from the impression and mounted on an articulator. The technician can now fabricate the provisional prosthesis on the mounted models. After it is completed the provisional prosthesis is cemented in place over the coping 26 using a temporary adhesive.

In each of the above embodiments, it is preferred that the provisional restorations be reinforced with reinforcement fibers or orthodontic wire, as appropriate.

The immediate provisional implants described above are intended to provide interim support for a multiple unit restoration for a period of several months. Typically, they will be used while permanent implants that have been simultaneously placed are submerged out of function during a period of osseointegration ranging from 3 to 6 months. The immediate provisional implants bear the load of temporary prostheses during this healing period while the permanent implants osseointegrate.

Though not necessary, the provisional implants are preferably removed at the time of or prior to the restoration of the permanent implants. Initially, the provisional prosthesis is removed from the implants. Any remaining temporary cement is removed from the top of the implants. The provisional implant retrieval tool is desirably placed into the ratchet adapter and ratchet. The retrieval tool is placed over the abutment of the provisional implant and the implant unscrewed by applying torque in a counter clockwise direction (for the illustrated thread orientation). After the implant is removed, a curette may be used to remove any associated granulation tissue. The soft tissue opening can be expected to close similar to a tooth extraction site. Alternatively, the provisional implants can be left in place and allowed to fully osseointegrate to the bone. In that case, only the portion of the provisional implants above the crestal bone are removed using a diamond burr. The exposed portions of the implant are then ground smooth with the crestal bone and the gums are sutured over the wound and allowed to heal.

While the components of the present invention have been described with a certain degree of particularity, it is manifest that many changes may be made in the specific designs, constructions and methodology hereinabove described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

I claim:

1. An immediate provisional dental implant elongated along an implant axis, comprising:
    an abutment adapted to bond with a dental prosthesis;
    a bendable neck segment connected to the abutment;
    a body segment connected to the flexible neck segment, the body segment having threads extending helically about the implant axis, the thread diameter tapering non-linearly from a maximum adjacent the neck segment to a minimum at a distal end;
    a torque engagement segment position below the flexible neck segment and above the body segment, said torque segment configured to engage a torque-imparting tool, said torque segment comprising at least one flat surface on an outer surface of the torque segment;
    wherein the abutment, bendable neck segment, body segment and torque engagement segment form a monolithic structure and the bendable neck segment is sufficiently bendable such that while the body segment is positioned with in a patient's jawbone the bendable neck segment can be bent to adjust the angle of the abutment.

2. The immediate provisional dental implant of claim 1, wherein the threaded body segment comprises an upper flared section proximal to the neck segment, an intermediate section and a tapered lower section distal from the neck segment, the lower section having a smaller angle of taper as compared to the upper section.

3. The immediate provisional dental implant of claim 2, wherein threads of the upper flared section define a taper angle between about 6° and 14°.

4. The immediate provisional dental implant of claim 2, wherein thread of the tapered lower section define a taper angle between about 3° and 7°.

5. The immediate provisional dental implant of claim 2, wherein the neck segment is more narrow than both of the upper flared section of the body segment and the abutment.

6. The immediate provisional dental implant of claim 2, wherein threads of the intermediate section have a constant diameter.

7. The immediate provisional dental implant of claim 1, wherein the thread diameter is within the range of about 1.0 mm and 3.5 mm.

8. The immediate provisional dental implant of claim 1, wherein the thread diameter is within the range of about 1.0 mm and 3.0 mm.

9. The immediate provisional dental implant of claim 1, wherein the body segment is at least about 12 mm in length.

10. The immediate provisional dental implant of claim 1, wherein a length of the body segment is approximately equal to the thickness of the cortical layer of the bone in which the implant is to be emplaced.

11. The immediate provisional dental implant of claim 1, wherein the neck segment and abutment form an extension from the body segment with a length of greater than about 3 mm.

12. The immediate provisional dental implant of claim 11, wherein the neck segment and abutment form an extension from the body segment with a length of greater than about 5 mm.

13. The immediate provisional dental implant of claim 1, having a total length along the implant axis of greater than 17 mm.

14. The immediate provisional dental implant of claim 13, having a total length along the implant axis of greater than 20 mm.

15. The immediate provisional dental implant of claim 1, having a thread depth tapering from a maximum thread depth adjacent the neck segment to a minimum thread depth adjacent the distal end.

16. The immediate provisional dental implant of claim 15, wherein the maximum thread depth is between about 0.5 mm and 0.7 mm.

17. The immediate provisional dental implant of claim 15, wherein a thread pitch of the body segment is in the range 0.8 mm to 1.8 mm.

18. The immediate provisional dental implant of claim 1, comprising a plurality of flat facets on the outer surface of the neck segment.

19. The immediate provisional dental implant of claim 1, consisting a material selected from the group consisting of titanium and alloys of titanium.

20. The immediate provisional dental implant of claim 1, wherein said torque engagement segment further comprises a plurality of flat surfaces configured to engage a wrench.

* * * * *